United States Patent
Walawalkar

[19]

[11] Patent Number: 5,904,685
[45] Date of Patent: *May 18, 1999

[54] SCREW SHEATH

[75] Inventor: Anuradha A. Walawalkar, Sunnyvale, Calif.

[73] Assignee: Stryker Corporation, Kalamazoo, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 08/843,038

[22] Filed: Apr. 11, 1997

[51] Int. Cl.⁶ .................................................. A61B 17/56
[52] U.S. Cl. ............................................. 606/73; 606/104
[58] Field of Search ................................ 606/73, 72, 104, 606/86, 60

[56] References Cited

U.S. PATENT DOCUMENTS

| | | | |
|---|---|---|---|
| 2,267,925 | 12/1941 | Johnston | 606/104 |
| 4,342,309 | 8/1982 | Eftekhar | 606/104 |
| 4,760,843 | 8/1988 | Fischer et al. | 606/73 |
| 4,963,144 | 10/1990 | Huene | 606/73 |
| 5,217,462 | 6/1993 | Asnis et al. | 606/73 |
| 5,354,292 | 10/1994 | Braeuer et al. | 606/1 |
| 5,443,509 | 8/1995 | Boucher et al. | 623/16 |
| 5,569,251 | 10/1996 | Baker et al. | 606/69 |
| 5,658,289 | 8/1997 | Boucher et al. | 606/73 |

*Primary Examiner*—Guy V. Tucker
*Attorney, Agent, or Firm*—Flynn, Thiel, Boutell & Tanis, P.C.

[57] ABSTRACT

An apparatus for endosteal fixation of a substitute graft by screw insertion having a cannulated sheath for guiding a screw into a tunnel in a surgical site. The sheath includes a tube section which has a protrusion on a cantilevered arm formed in the tube wall. The protrusion engages the external threads of the screw to lock the screw in position at a distal end of the sheath.

15 Claims, 3 Drawing Sheets

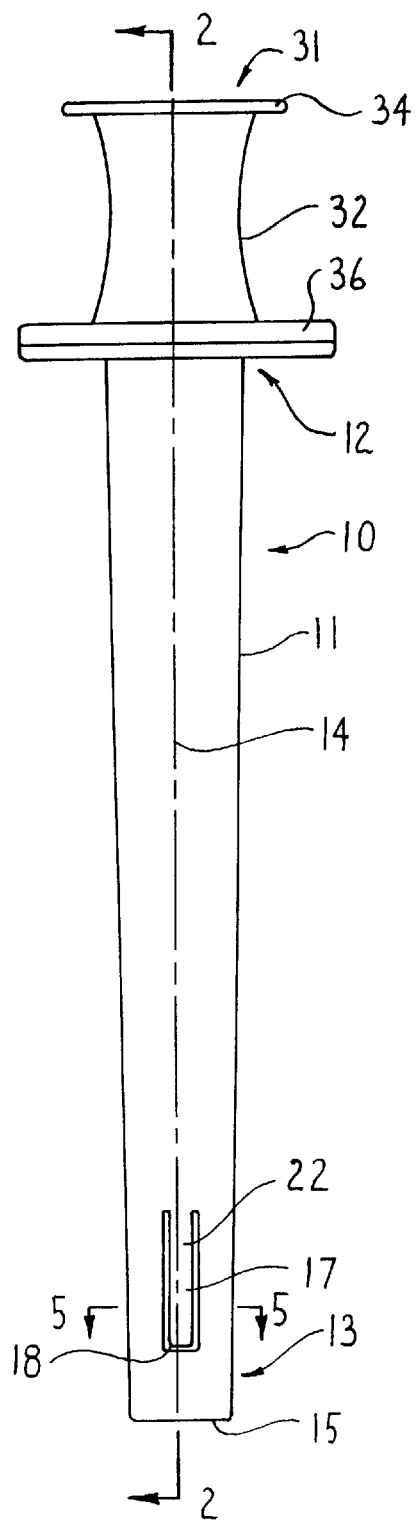
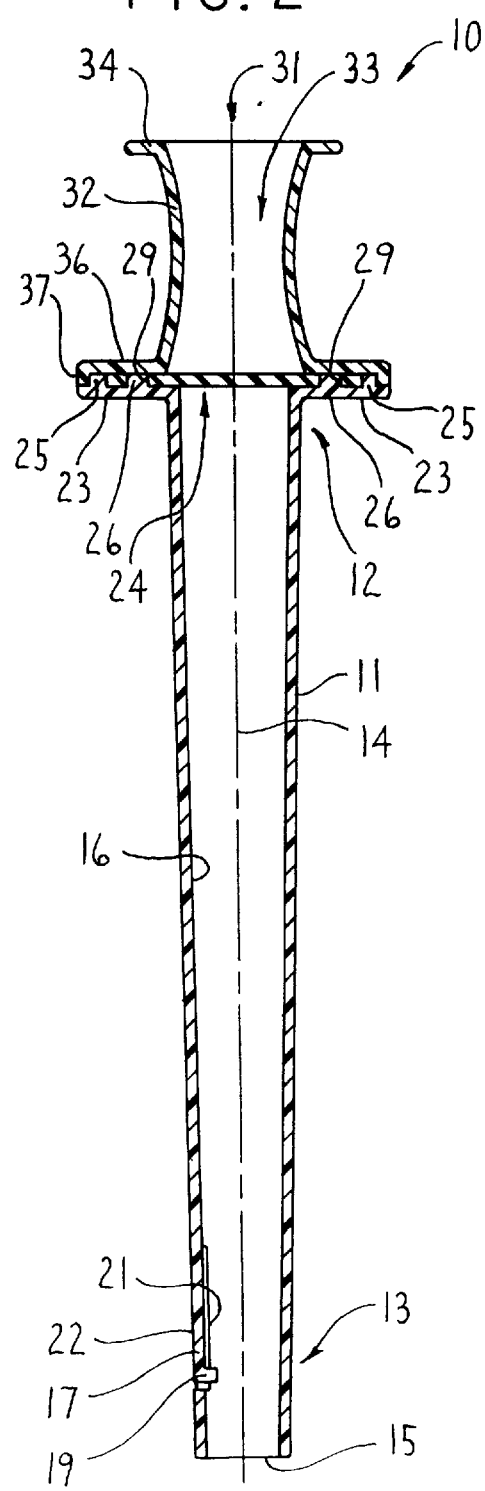

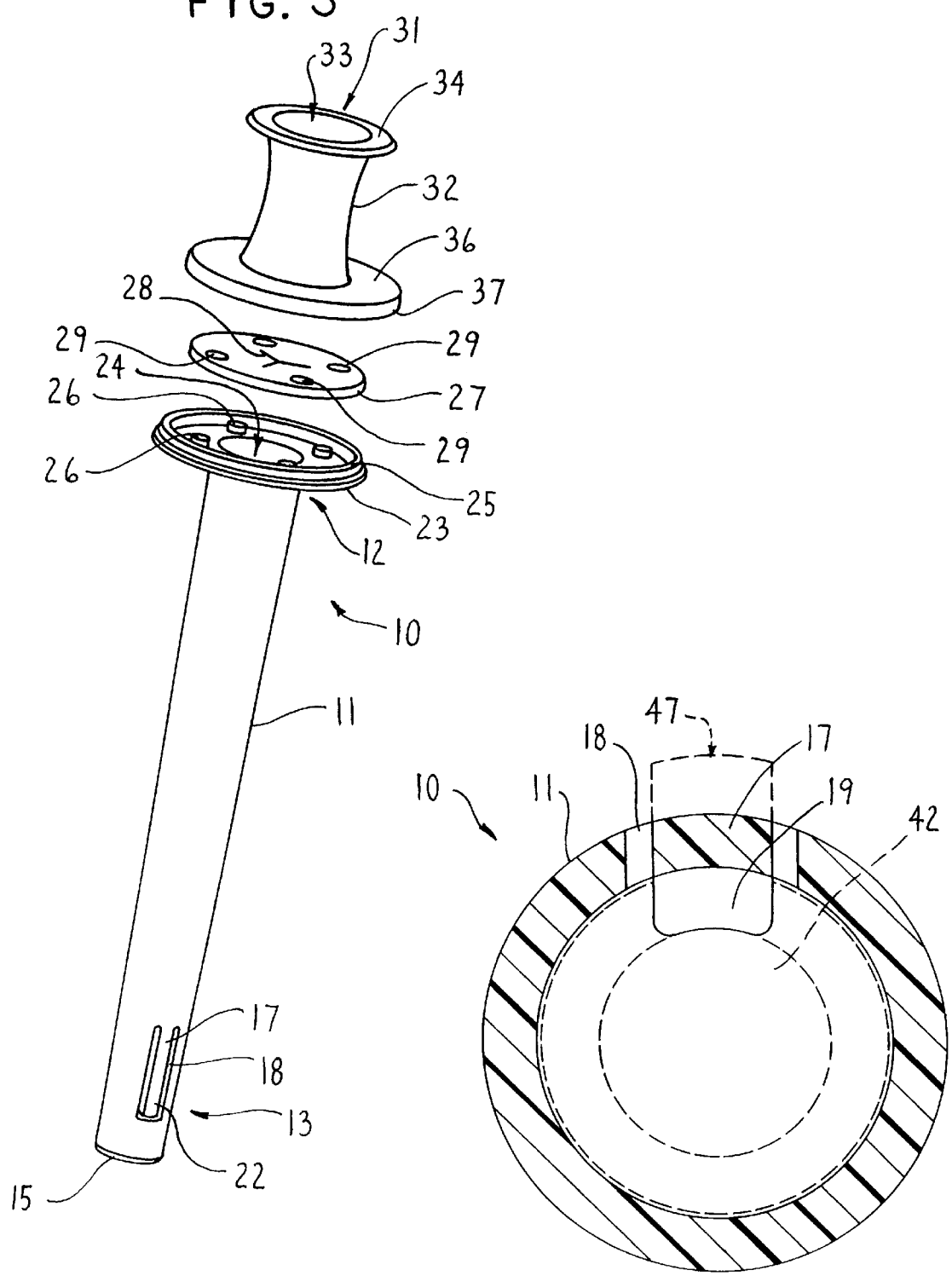

5,904,685

SCREW SHEATH

FIELD OF THE INVENTION

This invention relates to a surgical apparatus for performing an interference screw insertion for endosteal fixation of a ligament, and more particularly, a protective screw sheath for preventing collateral damage to surrounding tissue having a protrusion adjacent a distal end thereof guiding the interference screw for lengthwise movement within the protective sheath.

BACKGROUND OF THE INVENTION

During surgery to repair ligament and/or tendon damage, it is sometimes necessary to insert an interference or fixation screw into a bone. The screw provides a secure attachment for the repaired tissue or graft. However, screws may also damage the graft or the surrounding tissue during the insertion procedure. Protective devices, such as cannulated sheaths, are known which protect the surrounding tissue from undesired contact with the threads of the screw, thereby reducing collateral damage to the surgical site. The screw and a driver therefor are inserted into the hollow interior of the sheath. The screw is allowed to fall to the distal end of the sheath. The driver forces the screw out of the distal end of the sheath, however, the screw is free to move laterally and longitudinally within the distal end of the sheath. Other protective sheaths have a cut-out at the distal end exposing the threads of the screw to a graft tunnel in the surgical site and to surrounding tissue (see U.S. Pat. Nos. 5,211,647 and 5,425,733). This type of sheath may undesirably allow the threads of the screw extending through the cut-out to undesirably damage the graft or the surrounding tissue.

Accordingly, it is the object of the present invention to provide a screw sheath having a cannulated body which completely encloses the screw positioned therein until the screw exits the screw sheath and enters a tunnel in the surgical site, thereby preventing collateral damage to a graft or surrounding tissue by threads on the screw.

A further object of the invention is to provide a cannulated screw sheath, as aforesaid, with a protrusion extending into the hollow interior thereof, which protrusion engages the threads on the screw and secures the screw at a distal end of the screw sheath so as to prevent longitudinal movement of the screw therein absent rotary movement of the screw.

It is a further object of the invention to provide a screw sheath, as aforesaid, which is transparent to allow visual verification of the position of the screw within the screw sheath.

It is a further object of the invention to provide a screw sheath, as aforesaid, wherein the screw is secured at the distal end of the screw sheath without the threads thereof boring into the interior walls of the sheath to prevent the creation and deposit of shavings of the screw sheath material in the surgical site.

SUMMARY OF THE INVENTION

The present invention overcomes the above deficiencies by providing a sheath which encloses a screw and has a protuberance on the interior of the sheath which engages the threads of the screw to securely hold the screw therein. The screw being held within the sheath prevents the threads thereof from undesirably prematurely engaging the graft or surrounding tissue.

BRIEF DESCRIPTION OF THE DRAWINGS

Other features and advantages of the present invention will be apparent to persons acquainted with devices of this general type upon reading the following detailed description and inspecting the accompanying drawings in which:

FIG. 1 is a side view of a surgical apparatus, namely, a cannulated screw sheath for endosteal fixation of a substitute graft by a screw insertion embodying my invention;

FIG. 2 is a sectional view taken along the line 2—2 in FIG. 1;

FIG. 3 is an exploded view of the screw sheath;

FIG. 5 is a sectional view taken along the line 5—5 in FIG. 1.

DETAILED DESCRIPTION

Figure 4:
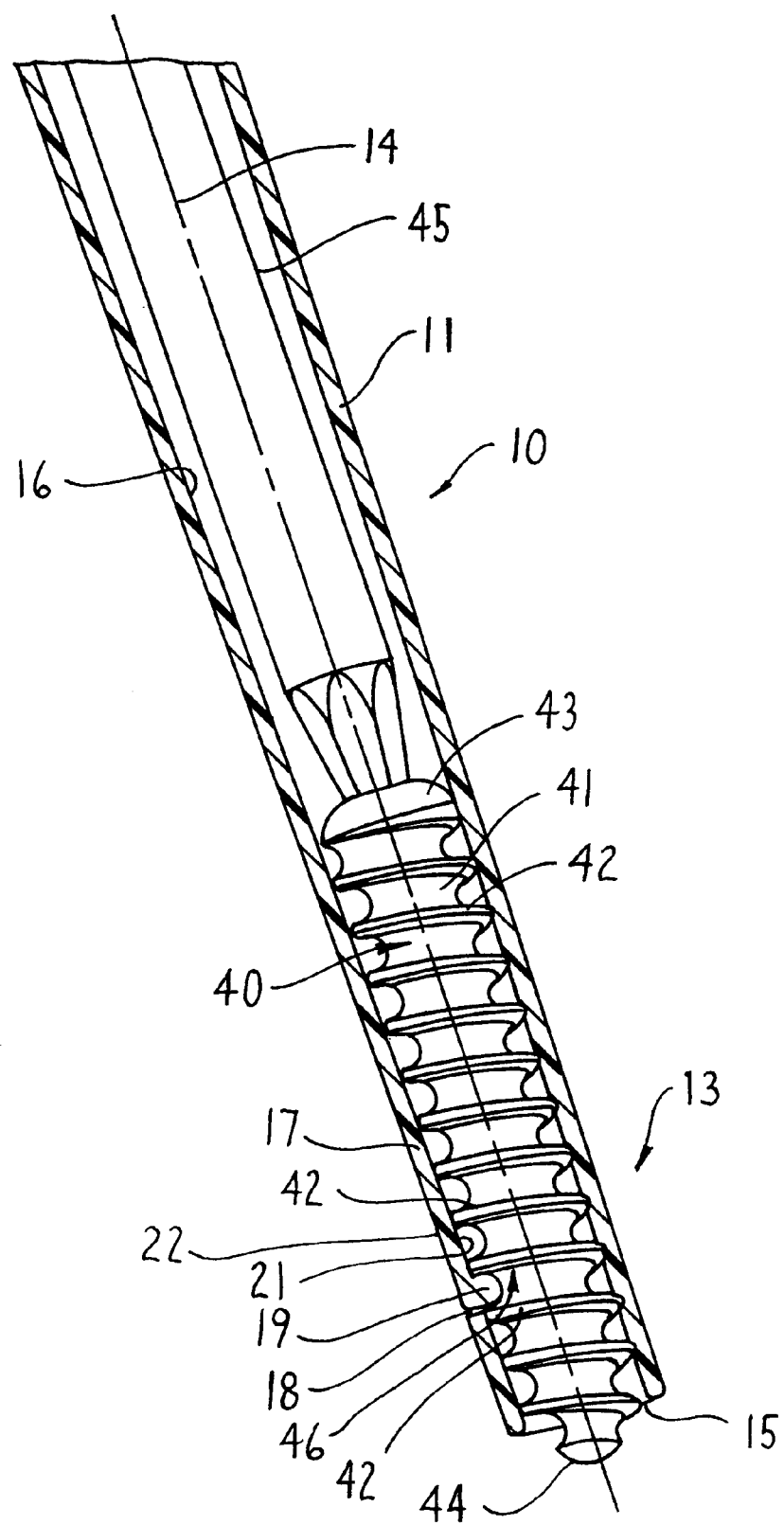
FIG. 4 is a partial cut-away view showing the screw sheath and protrusion with the screw and the driver inserted within the screw sheath.

The surgical apparatus of the present invention includes an elongate, generally cylindrical cannulated sheath 10 having a slightly tapered tube wall section 11 extending at about one-half degree to one degree from a proximal end 12 to a slightly smaller diameter distal end 13. The tapered wall section 11 encloses the interior 16 of the sheath 10. The elongate sheath 10 has a longitudinal axis through the center thereof as indicated at 14.

The cannulated sheath 10 is molded from a medical grade plastic with the tube wall 11 thereof being generally transparent. The transparent tube wall 11 allows a user to see into the interior of the sheath 10 and any screw oriented therein.

The distal end 13 terminates in an outward annular face 15. The face 15 is contained in a plane generally perpendicular to the longitudinal axis 14 of the sheath 10.

A U-shaped through slot 18 is provided in the tube wall 11 adjacent the distal end 13 so as to form an elastically yieldable, cantilevered arm 17 extending axially and coextensively with the tube wall 11. In this particular embodiment, the bight section of the U-shaped through slot 18 is adjacent the distal end 13 and the legs thereof are parallel to each other and extend from the lateral ends of the bight section toward the proximal end. In this embodiment, the cantilevered arm 17 is integrally molded within the structure of the tube wall 11 of the sheath 10. The arm 17 as an interior surface 21 facing into the interior 16 of the hollow sheath 10 and an exterior surface 22 facing outwardly. The interior and exterior surfaces 21, 22 are of the same curvature as the tube wall 11 and are generally flush with the respective interior and exterior wall surfaces of the tube wall 11. The proximal end of the cantilevered arm 17 is integral with the wall 11 of the sheath 10. The distal or free end of the cantilevered arm 17 is adjacent the bight section of the U-shaped through slot 18. The cantilevered arm 17 has a protrusion 19 at the free or distal end thereof. The protrusion 19 extends generally radially inwardly with respect to the sheath 10 and is positioned in a region adjacent the face 15 of the distal end 13.

The proximal end 12 of the wall section 11 of the sheath 10 has an enlarged circularly shaped, annular head or flange 23 extending outwardly generally transverse to the wall 11 of the sheath 10. The circular head 23 is generally disk-shaped encircling a central opening 24 constituting a proximal end of the hollow interior 16 of the sheath 10. An annular ridge 25 extends axially away from the circular head 23 on a side thereof remote from the distal end 13. The ridge 25 is circular and is positioned inwardly from the outer peripheral edge of the circular head 23. The circular head 23 also has plural axially projecting vertical posts 26 spaced radially inwardly from the ridge 25 and outwardly from the central opening 24. The posts 26 project in the same direction as does the ridge 25 and terminate in a plane flush with the terminal edge of the ridge 25.

A planar circular gasket or seal 27 is provided which is adapted to fit on the circular head 23 radially within the annular ridge 25. The seal 27 has plural slits 28 extending radially outwardly from a central point of the seal 27 toward the outer periphery thereof with the slits 28 being oriented generally within the confines of the central opening 24 of the circular head 23. The slits 28 extend through the thickness of the material of the seal 27 and are adapted to be axially displaced relative to the plane thereof to allow access through the seal 27 into the interior 16 of the sheath 10. Plural apertures 29 are positioned in the seal 27 adjacent the outer periphery thereof and each thereof is shaped to receive a respective post 26 therein to stationarily position the seal on the circular head 23. The seal 27 is constructed from a medical grade elastomer.

A hollow handle 31 is provided to securely hold the seal 27 onto the circular head 23 and provide a secure gripping area for a user. More specifically, the handle 31 has a cylindrical wall 32 cambered inwardly at the center thereof to define a hollow interior 33 therein. The hollow interior 33 is axially aligned with the central opening 24 of the circular head 23 and is generally coaxial with the longitudinal axis 14 of the elongate sheath 10. An annular flange 34 extends radially outwardly from an axial end of the handle 31 remote from the tube 11. The flange 34 acts as a stop to prevent the fingers of a user from slipping off the end of the handle 31. A further radially outward flange 36 extends from the other axial end of the wall 32 of the handle 31 proximal the tube 11. The flange 36 has an annular ridge 37 extending transverse to and axially therefrom toward the annular head 23. The annular ridge 37 is adapted to rest adjacent the annular ridge 24 of the circular head 23 on the radially outside thereof. The ridges 24, 37 overlap each other and secure the handle 31 onto the circular head 23 as, for example, by a snap fit by radially pressing against one another. Alternatively, adhesive may be used to secure the handle 31 onto the circular head 23, for example at the ridges 24, 37. The handle 31 is also molded from a medical grade plastic.

Referring now to FIG. 4, the cannulated sheath 10 receives a screw 40 therein for fixation or insertion into a surgical site. The screw 40 has a central core 41 and external threads 42 extending radially and spirally outwardly from the central core 41. The core 41 and the external threads 42 of the screw 40 travel freely through the hollow interior of the sheath 10, except where the protrusion 19 positioned on the cantilevered arm 17 extends radially inwardly into the interior 16 of the tube wall 11 of the sheath 10. When the screw 40 is rotated, the threads 42 threadedly to mesh or interlock with protrusion 19. The distal end of the protrusion 19 has a shape generally corresponding to the root region 46 between mutually adjacent flanks of the threads 42.

The screw 40 has a conventional head or trailing end 43 with a polygon shaped socket therein which receives a driver 45 with a conventional tip or front end 44 therein. As shown in FIG. 4, the leading end 44 is tapered relative to the rest of the screw to define a smaller diameter core and threads allowing the screw to self thread into a pilot hole at the surgical site and onto the protrusion 19. It is common in this field to use a hex driver receivable within a hex socket (not shown) in the head 43 of the screw 40 as the driver 45. It is preferable that the cantilevered arm 17 be sufficiently resistant to axial compression and tension to cause the screw 40 to move axially of the sheath in response to a rotation of the screw. It is also preferable that the maximum outside diameter of the screw 40 can be less than the minimal diameter of the interior 16 without detracting from the thread relation of the protrusion 19 with the external threads 42 on the screw.

OPERATION

Although the operation of the inventive sheath will be understood from the foregoing description by skilled persons, a summary of such description is now given for convenience. The cannulated sheath 10 is used to insert a usually metal screw 40 for endosteal fixation of a graft. A screw 40 is placed into the hollow interior 33 of the handle 31. The screw 40 will rest on the top of the seal 27 until force is applied to the screw 40 which forces the screw 40 through the slits 28 in the seal 27. Due to the force applied, the slits 28 are axially displaced and create an opening through the seal 27 for the screw 40 and driver 45. The seal 27 will prevent the screw 40 from exiting the cannulated sheath 10 through the handle 31. The screw 40 will fall toward the distal end 13 when the sheath 10 is held upright. The driver 45 is also inserted through the opening created by the slits 28.

When the screw 40 is adjacent the distal end 13 of the sheath 10, the protrusion 19, in particular the side facing the proximal end, engages a side of a thread 41 facing the distal end 13. Thus, the protrusion 19 acts as a locking mechanism securing the screw at the distal end 13 of the sheath 10. The protrusion 19 and tube wall 11 act to prevent and at least reduce significant lateral movement of the screw 40 within the distal end 13 thereby assisting in accurate placement of the screw in the surgical site. The threads 41 are conventionally shaped so that when the screw 40 is rotated clockwise by likewise rotating the driver 45 engaging the screw, the screw 40 moves lengthwise in the interior of the sheath 10 and forwardly out of the distal end 13. The sheath 10 is preferably transparent so that the positioning of the screw 40 may be visually verified through the tube wall 11 of the sheath 10. To back the screw longitudinally away from the face 15 of the distal end 13, the screw is turned counter-clockwise. The protrusion 19 prevents the screw from slipping longitudinally out of the sheath 10 through the face 15 while maintaining the threads completely within the sheath thereby preventing unwanted damage to the graft or surrounding tissue until the screw enters a tunnel at the surgical site.

The protrusion 19 and the arm 17 are adapted to accommodate screws 40 having central cores 41 with varying diameters. If the central core 41 of a screw 40 occupies more width within the interior of the sheath 10 than the width between the protrusion 19 and the portion of the wall 11 opposite the protrusion 19, the central core 41 displaces the protrusion 19 on the elastic arm 17 radially outwardly as depicted at 47 in broken lines in FIG. 5. This allows the central core 41 to pass by the protrusion 19 while allowing screws 40 with varying central core widths or manufacturing tolerances to be used within the cannulated sheath 10.

When the screw has a head 43 lacking threads, the head must also pass over the protrusion 19. The protrusion 19 is positioned on the cantilevered arm 17 so that the head 43 of the screw 40 as it passes by the protrusion 19 forces the resilient arm 17 to flex or yield radially away from the screw 40 thereby allowing the screw head 43 to pass the protrusion 19. While a headed screw is illustrated, this apparatus also operates with a headless screw.

The seal 27 between the sheath 10 and the handle 31 prevents liquid from leaching through the sheath 10 and out of the end of the handle 31.

Although a particular preferred embodiment of the invention has been disclosed in detail for illustrative purposes. It will be recognized that variation or modification of the apparatus including the rearrangement of parts lie within the scope of the present invention. For example, the cantilevered arm with the protrusion thereon could extend in a direction other than solely longitudinally of the sheath.

The embodiments of the invention in which an exclusive property or privilege is claimed are defined as follows:

1. An apparatus for endosteal fixation of a substitute graft to bone by screw insertion, comprising:

an elongated screw having a front end, a back end and an external thread; and an elongated and hollow sheath solely adapted for manual guiding of said screw to a specific location in a surgical site while preventing collateral damage to a substitute graft and surrounding tissue by the threads on said screw, said sheath having a proximal end and a distal end, a region of said sheath more close to said distal end than said proximal end including means defining a protrusion on an interior surface of said hollow sheath, said screw oriented in said interior of said sheath threadedly engaging said protrusion defining means so that a rotation of said screw relative to said sheath will cause said screw to move lengthwise in said interior of said sheath and out of said distal end of said sheath and into thread engaging relation with the substitute graft and bone so as to enable a manual removal of said sheath from the surgical site, said protrusion defining means including an elongate arm formed in a wall of said sheath, a proximal end of said arm being integral with said wall of said sheath and a remainder of said arm being separated from said wall and extending axially of said sheath to a distal end whereat said protrusion extends into said interior of said hollow sheath.

2. The apparatus according to claim 1, wherein said arm has an exterior surface and an interior surface, both of which are flush with respective exterior and interior wall surfaces on said sheath.

3. The apparatus according to claim 1, wherein said screw has a central core, said external thread projecting radially outwardly from said core; and wherein said protrusion defining means includes a region conforming to an external surface of said core between mutually threaded flanks of said external thread.

4. The apparatus according to claim 1, wherein said arm is elastically yieldable in directions radially of said sheath.

5. The apparatus according to claim 4, wherein said screw has a central core, said external thread projecting radially outwardly from said core; and wherein said protrusion defining means includes a region conforming to an external surface of said core between mutually threaded flanks of said external thread, whereby tolerance variations in a diameter of said external surface of said core will be accommodated by said elastically yieldable characteristic of said arm.

6. The apparatus according to claim 1, wherein said protrusion defining means is oriented sufficiently close to said distal end so that said screw will exit said distal end while remaining threadedly engaged with said protrusion defining means.

7. The apparatus according to claim 1, wherein said arm is sufficiently resistant to axial compression and tension to cause said screw to unyieldingly move axially of said sheath in response to said rotation of said screw.

8. The apparatus according to claim 1, wherein said screw has a headed end without an external thread thereabout generally equal in outer diameter to an outer diameter of said external thread immediately adjacent thereto; and wherein said protrusion is elastically yieldable in a radially outward direction so that said head end of said screw can move past said protrusion defining means.

9. The apparatus according to claim 1 wherein said distal end of said elongate sheath terminates in a face lying in a plane perpendicular to a longitudinal axis of said elongated sheath.

10. An apparatus for endosteal fixation of a substitute graft by screw insertion, comprising:

a cannulated sheath having a wall structure configured to enclose a majority of a length of an externally threaded screw and being solely adapted for manual guiding of the externally threaded screw to a specific location in a surgical site while preventing collateral damage to a substitute graft and surrounding tissue by the threads on said screw, said cannulated sheath additionally having a proximal end and a distal end and an internal protrusion on said wall structure adjacent said distal end;

an externally threaded screw adapted to be received in said sheath, the external threads on said screw being engagable with said internal protrusion while a majority of the screw threads are simultaneously completely shielded by said wall structure from adjacent substitute graft and tissue at the surgical site, said screw moving longitudinally within said distal end of said sheath in response to a rotational movement of said threads on said internal protrusion;

tool coupling means on an axial end of said screw remote from said distal end of said sheath for facilitating a rotating driving coupling from said tool to said screw; and a screw driver tool having a screw engaging means thereon for coupling engagement with said tool coupling means on said screw, said screw driver tool being adapted for reception in said proximal end of said cannulated sheath to engage and couple to said tool coupling means to enable said screw driver tool to impart a rotation of said screw relative to said sheath and said protrusion and a movement completely out of said distal end of said sheath so as to enable a manual removal of said sheath from the surgical site.

11. A method of endosteal fixation of a substitute graft by screw insertion, comprising the steps of:

longitudinally inserting a screw into an elongate and hollow sheath to enclose the threads of the screw within the sheath;

threadedly engaging the threads with a protrusion positioned on the interior of the hollow sheath thereby preventing further longitudinal movement of the screw within the sheath;

positioning a distal end of the sheath within the surgical site to align the screw with a tunnel hole in the surgical site; and rotating the threads of the screw relative to the protrusion causing longitudinal movement of the screw out of the sheath.

12. The method according to claim 11, further comprising the step of laterally displacing the protrusion to allow a head of the screw to pass thereby.

13. The method according to claim 11, wherein the step of positioning the distal end of the sheath includes visually affirming the location of the screw within the sheath by viewing the screw through a wall of the sheath.

14. The method according to claim 11, wherein the step of rotating the threads includes the step of exiting the screw from the distal end of the sheath while continually engaging the protrusion.

15. The method according to claim 11, wherein the enclosing of the threads includes the step of preventing the threads from engaging the graft and the surrounding soft tissue until after the screw begins to exit the distal end.

* * * * *